(12) United States Patent
Rohanizadeh et al.

(10) Patent No.: US 7,785,648 B2
(45) Date of Patent: Aug. 31, 2010

(54) ADHERENT APATITE COATING ON TITANIUM SUBSTRATE USING CHEMICAL DEPOSITION

(75) Inventors: Ramin Rohanizadeh, Surry Hills (AU); Racquel Z. LeGeros, New York, NY (US)

(73) Assignee: New York University, New York, NY (US)

( * ) Notice: Subject to any disclaimer, the term of this patent is extended or adjusted under 35 U.S.C. 154(b) by 977 days.

(21) Appl. No.: 11/232,420

(22) Filed: Sep. 21, 2005

(65) Prior Publication Data
US 2006/0062925 A1 Mar. 23, 2006

Related U.S. Application Data

(60) Provisional application No. 60/612,063, filed on Sep. 22, 2004.

(51) Int. Cl.
*B05D 1/18* (2006.01)
*A61L 27/32* (2006.01)
*A61K 6/083* (2006.01)

(52) U.S. Cl. ............... 427/2.1; 427/2.24; 427/2.25; 427/2.26; 427/2.27; 427/2.28; 427/430.1

(58) Field of Classification Search ............ 427/2.1, 427/2.24, 2.25–2.27, 430.1
See application file for complete search history.

(56) References Cited

U.S. PATENT DOCUMENTS

| | | |
|---|---|---|
| 4,880,610 A | 11/1989 | Constantz |
| 4,965,088 A | 10/1990 | Shimamune et al. |
| 5,141,576 A | 8/1992 | Shimamune et al. |
| 5,205,921 A | 4/1993 | Shirkanzadeh |
| 5,211,833 A | 5/1993 | Shirkhanzadeh |
| 5,258,044 A | 11/1993 | Lee |
| 5,279,831 A | 1/1994 | Constantz et al. |
| 5,612,049 A | 3/1997 | Li et al. |
| 6,069,295 A | 5/2000 | Leitao |
| 6,153,266 A | 11/2000 | Yokogawa et al. |
| 6,207,218 B1 | 3/2001 | Layrolle et al. |
| 6,280,789 B1 | 8/2001 | Rey et al. |
| 6,331,312 B1 | 12/2001 | Lee et al. |
| 6,428,803 B1 | 8/2002 | Ewers et al. |
| 6,974,532 B2 * | 12/2005 | LeGeros et al. ............ 205/108 |

OTHER PUBLICATIONS

Y. Fujishir et al. Coating of hydroxyapatite on various substrates via hydrothermal reactions of Ca(edta02- and phosphate. 2001. Jounal of materials Science: Materials in Medicine. vol. 12 pp. 333-337.*

(Continued)

*Primary Examiner*—Timothy H Meeks
*Assistant Examiner*—Cachet I Sellman
(74) *Attorney, Agent, or Firm*—Klauber & Jackson, LLC

(57) ABSTRACT

An adherent bioactive calcium phosphate coating is formed on a titanium or titanium alloy substrate by immersing the substrate in an acidic calcium phosphate solution to form a non-apatitic calcium phosphate coating on the substrate. In a second step the coated substrate can be converted to a less reactive coating by being immersed into a basic or neutral solution to convert the coating into an apatite. However if a relatively reactive coating is desired, the second step can be dispensed with.

22 Claims, 9 Drawing Sheets

OTHER PUBLICATIONS

Silva et al. "Transformation of monetite to hydroxyapatite in bioactive coatings in titanium". 2001. Surface and Coatings Technology vol. 137. pp. 270-276.*

Okido et al. "Hydroxyapatite coating on titanium by means of thermal substrate method in aqueous solutions." 2002. Solid State Ionics vol. 151 pp. 47-52.*

* cited by examiner

ADHERENT APATITE COATING ON TITANIUM SUBSTRATE USING CHEMICAL DEPOSITION

RELATED APPLICATION

This application claims priority from U.S. Provisional Application Ser. No. 60/612,063, filed Sep. 22, 2004.

FIELD OF INVENTION

This invention relates generally to the manufacture of orthopedic and dental implants, and more specifically relates to a process for chemical disposition of a bioactive calcium phosphate coating on the Ti and Ti alloys which are the metals of choice for fabrication of such implants.

BACKGROUND OF INVENTION

Commercially pure titanium (Ti) and Ti alloys are the metals of choice in orthopedic and dental applications because of their biocompatibility, resistance to corrosion and good mechanical properties such as lightweight, durability, high strength, and the ability to be prepared in different forms, shapes and textures. However, Ti or Ti alloy do not directly bond or attach to bone. Instead, there is a layer of fibrous tissue at the Ti-bone interface causing a weak interface that could increase the possibility of the implant loosening over a long period of time. On the other hand, materials such as calcium phosphate materials (e.g., hydroxyapatite, HA; tricalcium phosphate, β-TCP; and biphasic calcium phosphate, BCP), are bioactive, forming a direct bond and a uniquely strong interface with bone, but are not strong enough for load-bearing areas.

Commercial dental and orthopedic implants coated with plasma-sprayed HA were developed to combine the strength and superior mechanical properties of the metal (Ti or Ti alloy) and the bioactivity and osteoconductivity of the Ca—P compounds. Better bonding and fixation between implant and host tissue minimize the micro-movements that promote fibrous tissues formation at the implant/tissue interface and may cause implant failure. Coating with Ca—P materials was also shown to inhibit the release of substrate metal ions (Ti, Al, V) from substrate, ions that may be potentially harmful to cells and/or may interfere with the biomineralization process. There are, however, some shortcomings of the plasma-sprayed HA coating. Xray diffraction analyses of plasma-sprayed HA dental and orthopedic implants showed variable coating composition and surface morphology. The coatings were shown e.g., to consist of crystalline (principally HA) and non-crystalline (amorphous calcium phosphate, ACP) phases. The HA/ACP ratio in the coating varied from 30/70 to 70/30. [LeGeros R Z, LeGeros J P, Kim Y, Kijkowska R, Zheng R, Bautista C, Wong J L. Calcium phosphates in plasma-sprayed HA coatings. Ceramic Trans 48:173-189, 1995. LeGeros R Z, Kim YE, Kijkowska R, Zurita V, Bleiwas C, Yuang P-Y, Edwards B, Dimaano F, LeGeros J P. HA/ACP ratios in calcium phosphate coatings on dental and orthopedic implants: Effect on properties. Bioceramics 11. Singapore: World Scientific Publishing Co., pp 181-184, 1998.] The coating composition also differed from the coating layer closest to and away from the metal substrate and was also affected by the geometry of the implant. [LeGeros J P, Huang P Y, LeGeros R Z, Wong J L. Effect of substrate geometry on heat capacity and crystallinity on plasma-sprayed HA coatings. J Dent Res 1998; 77:2682.] ACP is much more soluble than HA, therefore the dissolution (or biodegradation) of the coating is very much affected by the HA/ACP ratio in the coating: the lower the ratio, the greater the rate of biodegradation. Some additional phases such as β-tricalcium phosphate (β-TCP), α-TCP, tetracalcium phosphate (TeTCP), and sometimes calcium oxide are also formed during the high temperature process of plasma spraying. Like ACP, these additional phases have higher solubility than HA. The uneven biodegradation of coating can result in a non-homogenous bone bonding or bone growth around the implant and/or delamination and separation of big fragments or debris from the coating materials that can cause premature disintegration of the coating—and severe complication in the osseointegration of the implant.

Osteogenic macromolecules (e.g., bone morphogenetic proteins (BMPs), bioactive peptides or proteins, and bone growth factors) have been shown to improve and increase the extent of bone formation. Coating on metallic implant can be also used as an effective carrier to deliver and release the osteogenic molecules to the site of implantation. To allow controlled release of bioactive molecules, their incorporation must be achieved during the coating procedure which requires physiological temperatures (37° C.). The incompatibility of the extremely high temperatures (about 30,000° C.) associated with the plasma spray method is obvious. In addition, the plasma-spray method, being a line-of sight technique,—will not provide uniform coating on complex shaped materials with internal cavities or macroporosities.

Because of the above-mentioned disadvantages of the plasma spray method, the potential of in situ Ca—P coating methods are being extensively explored. Three principal low-temperature coating methods are: (i) chemical deposition of Ca—P compounds by immersion of Ti or Ti alloy substrate in a calcifying solution containing Ca and P ions (chemical or biomimetic deposition); (ii) formation of Ca—P layer on substrates using sol-gel processing; and (iii) Ca—P coating using electrodeposition (ECD) method. Most of the coatings obtained by these methods do not give the shear and tensile strength comparable to that obtained by the plasma-spray method. Recently too, one of the present inventors and her colleagues reported a pulse-modulated ECD method of depositing octacalcium phosphate [Lin S, LeGeros R Z, LeGEros J P. Adherent octacalcium phospahte coating on titanium alloy using modulated electrochemical deposition method. J Biomed Mater Res 66A:819-828, 2003.] and calcium-deficient, carbonate-substituted and fluoride substituted apatite coatings with strength comparable to that obtained with the plasma-spray method [LeGeros J P, Lin S, LeGeros R Z. Electrochemically deposited calcium phosphate coating on titanium alloy. J Dent Res 79:560, 2000 (abstr no. 560.].

In order to enhance the adhesion and the coverage of Ca—P coating, several studies explored chemical and/or mechanical pre-treatment of the Ti or Ti alloy surfaces. Formation of bioactive $TiO_2$ hydrogel layer has been shown to improve the nucleation of calcium phosphate during chemical deposition. $TiO_2$ layer can be prepared by alkaline, $H_2O_2$, sol-gel or heat treatment methods. Kokubo and his collaborators [Wei M, Kim H M, Kokubo T, Evans J H. Optimising the bioactivity of alkaline-treated titanium alloy. Mat Sci Eng C-Bio S 20:125-134, 2002; Kim H M, Kokubo T, Fujibayashi S, Nishiguchi S, Nakamura T. Bioactive macroporous titanium surface layer on titanium substrate. J Biomed Mater Res 52:553-557, 2000. Takadama H, Kim H M, Kokubo T, Nakamura T. An X-ray photoelectron spectroscopy study of the process of apatite formation on bioactive titanium metal. J Biomed Mater Res 55:185-193, 2001.] demonstrated that the treatment of Ti with a NaOH solution followed by heat treatment at 600° C. forms a crystalline phase of sodium titanate layer on the Ti surface resulting in improved adhesion of apatite coating prepared by incubation in simulated body fluid (SBF). The authors concluded that release of the sodium ions from the sodium titanate layer causes formation of Ti—OH groups which react with the calcium ions from the SBF and form calcium titanate which then could act as nucleation sites for apatite crystal formation. Alkali treatment results in the formation of $TiO_2$ layer leading to a negatively charged surface which in turn attracts cations such as calcium ions. Etching with acid followed by alkali treatment was also investigated to combine the surface roughness increase due to acid treatment and formation of $TiO_2$ bioactive layer. $TiO_2$ could be also prepared using $H_2O_2$ alone or mixture of acid/$H_2O_2$ or metal chlorides/$H_2O_2$ solutions.

SUMMARY OF INVENTION

Now in accordance with the present invention a chemical deposition method has been found that will provide higher coating attachment and coverage. In many instances the method of the invention is carried out in two steps. However if a relatively reactive coating is desired, the second step can be dispensed with. In the general mode of practicing the initial step (step one), an adherent bioactive calcium phosphate coating is formed on a titanium or titanium alloy substrate by immersing the said substrate in an acidic calcium phosphate solution to form a non-apatitic calcium phosphate coating on the substrate. The calcifying solution will include a mixture of a calcium salt and a phosphate compound together with an acidifying agent as required. The range of the Ca/P molar ratio in the calcifying solution should be from about 1/1 to 3/1. Depending on the temperature and pH conditions, the resulting non-apatitic calcium phosphate coating is one or more calcium phosphate compounds such as DCPD (dicalcium phosphate dihydrate, $CaHPO_4.2H_2O$); DCPA (dicalcium phosphate anhydrous, $CaHPO_4$, monetite); and/or OCP (octacalcium phosphate, $Ca_8H_2(PO4)_6.5H_2O$). DCPD, DCPA and OCP are reactive compounds (with DCPD being the most reactive), converting to biological apatite in vivo. If a reactive coating is desired, there is no need to go to the second step (step two). If a less reactive coating is desired in step one, the calcifying solution can be modified by adding fluoride ion, e.g. as NaF.

If the initial coating from step one is to be converted to a less reactive apatite coating (such as apatite, carbonate-containing or F-containing apatite) then in step two the coated substrate from step one is immersed into a basic or neutral solution to convert the coating into an apatite.

In conducting step one, the pH range will generally be from about 2.1 to less than 7, with a pH of 2.1 to 5 being preferable. The temperature will generally range from 25° to 75° degrees C., with a preferable range being from 25° to 40° degrees C. (at which principally DCPD is produced). The time of immersion in step one will vary in accordance with the desired coating thickness. For most applications the immersion time will be from about 2 to 24 hours.

Where step two is carried out the solution used to effect conversion to a less reactive apatite can have a pH of from about 7 to 12, and a temperature of from about ambient (around 25° C.) to around 70° C. The conversion media can include alkaline compounds such as NaOH or KOH, $NaHCO_3$ (or $KHCO_3$), and NaF (or KF) if fluoride ions are desired. The media can also include other salts providing such ions as those of Mg, Zn etc. The substrate from step one will typically be immersed in the solution of step two for from 2 to 24 hours.

Where two consecutive steps are used, they thus involve (1) deposition of a monetite ($CaHPO_4$) coating by immersing the Ti substrates in an acidic Ca—P solution (using phosphoric acid), followed by (2) transformation of monetite to apatite using a basic solution or neutral solution. Using acidic Ca—P solution as the calcifying solution has three advantages: It permits a higher concentration of the calcium and phosphate ions in the calcifying solution; it enables etching of the titanium surface; and it makes a positive surface charge that leads to attraction of anions such as phosphate ($H_2PO_4^-$, $HPO_4^{2-}$, $PO_4^{3-}$) and therefore increases the coating/substrate interfacial strength. In tests, the apatite coating obtained from this two-step procedure is found to be uniform in composition, structure and thickness and to provide 100% coverage on the substrate. The tensile bond of the apatite coating was 5.2 MPa and its adhesion was measured at 13.1N using a scratch test. Calcium and phosphorus elements were detected on Ti surface after the coating was removed using tensile or scratch test, revealing the formation of adherent calcium phosphate layer at the coating/substrate interface. The two-step chemical coating method for depositing apatite on titanium substrate is simple and low cost. It produces an apatite coating that is adherent and very homogenous compared to coatings produced via other low temperature coating methods.

This coating method deposits an adherent bioactive calcium phosphate coating on titanium implants at low temperature. The method produces a uniform coating surface property and composition even on substrates with complex geometry (macroporosity or internal cavities). The method is simple and very low cost and allows the incorporation and delivery of osteogenic macromolecules (e.g. bone morphogenetic proteins) that leads to the improvement of bone formation and stability of the implant. The method will improve the success rate of dental or orthopedic metallic implants.

Compared to the other in situ techniques at low temperature the present two step method has the following advantages and innovations:

(1) Using an acidic calcifying solution results in a positive charge on the titanium surface due to the formation of $[Ti—OH_2]^+$ groups. Positive surface charge attracts phosphate groups during the coating process, which provides sites for nucleation and growth of Ca—P crystals and, therefore increases the adhesion and coverage of the coating on substrate.

(2) The lower pH of the calcifying solution permits the use of a higher concentration of calcium and phosphate ions in the solution. In a neutral calcifying solution (pH 7), the concentrations of calcium and phosphate ions are limited and at higher concentrations, Ca—P crystals start to precipitate in the solution. Using a calcifying solution with a higher concentration of calcium and phosphate ions results in a faster and better coverage of the coating.

(3) Acidic calcifying solution creates etching pits and increases the surface roughness of titanium, which leads to a better mechanical interlock between coating and Ti substrate.

(4) Once the adherent Ca—P phase is deposited on titanium surface, it can be transformed to apatitic structure by immersing in a basic or physiological condition (e.g. at pH 7.4 and 37° C.) solution. At this stage of the coating process, osteogenic macromolecules such as Bone Morphogenetic Proteins (BMPs) could be incorporated into the coating material, which in turn improves the stability and recovery post-operation time.

DESCRIPTION OF PREFERRED EMBODIMENT

Figure 1:
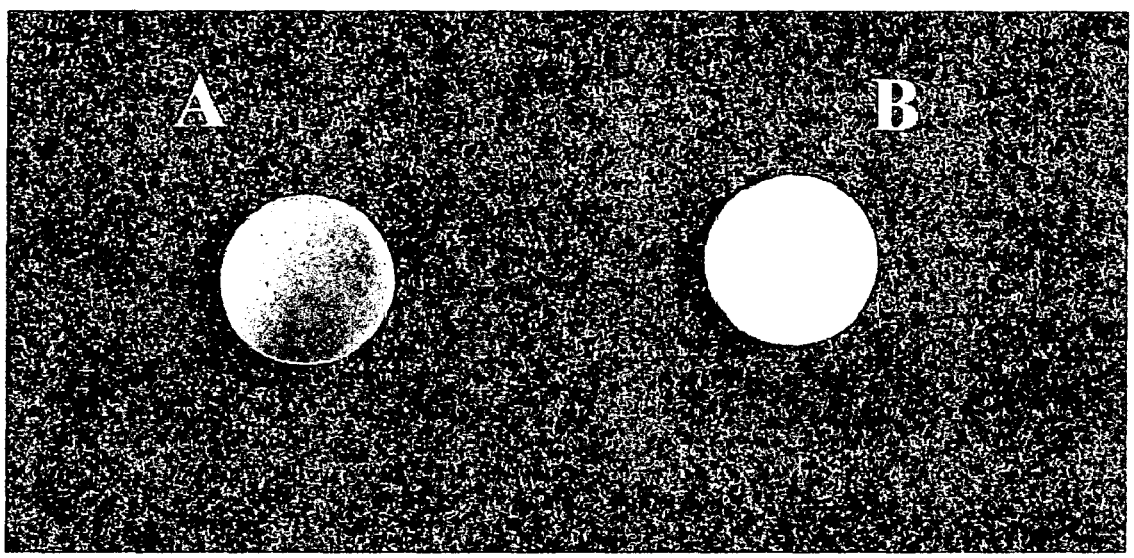
FIG. 1 is an SEM of (A) uncoated and (B) apatite coated Ti discs.

Sample Preparation: Sixty commercially pure titanium (Cp-Ti, ASTM B-265) discs (2 mm thickness and 12.7 mm diameter) were polished with 320, 400, and 600 grit papers using a grinding machine (Buehler, Phoenix Beta), ultrasonically cleaned in baths of doubly distilled (ddw), acetone, ddw, ethanol, and ddw (10 min in each bath), and then air-dried.

Two Step Apatite coating: the discs were immersed in a calcifying solution prepared by mixing 200 mM $CaCO_3$+100 mM $NaH_2PO_4.H_2O$ and dissolving the mixed reagents with 2.9% $H_3PO_4$ solution. The pH of the solution was 2.67 at room temperature. The discs were placed on the bottom of a sealed container and kept in oven at 75° C. for 24 h. 10 discs were placed in each container with 100 ml of calcifying solution. The discs were then removed from the solution, rinsed three times in distilled water, and air-dried. After removing the discs, the pH of the calcifying solution was 2.81 at room temperature. In the second step, to convert the Ca—P phase (monetite) formed from the first step to apatite, the discs were immersed in the 0.2M NaOH solution at 75° C. for 24 h. These parameters were chosen based on results of several pilot studies. The discs were then removed from the NaOH solution, rinsed three times in ddw, and the air-dried.

Analytical Methods:

Scanning Electron Microscopy (SEM) and Electron Dispersive Spectroscopy (EDS): The shape, size, and coverage of Ca—P crystals formed from acidic solution and then their transformation to apatite crystals were analyzed using SEM (Jeol-5400) operating at 20 kV. An EVAX microanalysis system (EDS) coupled to SEM was used to determine the chemical elements of the coating materials in each step of coating procedure. After removing the coating materials using tensile or scratch tester, EDS analysis was also carried out on the titanium surface or on the residual coating on substrate. The specimens were coated with gold-palladium prior to SEM observation and carbon for EDS analysis. One way-Anova and Tukey statistical tests were used to compare the percentage and ratios of different chemical elements in different areas of the coating.

X-ray diffraction (XRD): X-ray diffraction (Philips X'Pert) using grazing incident angle of 2° was performed to determine the structural and chemical modification on the Ti surface after each step of the coating procedure. XRD was carried out using $CuK_\alpha$ radiation operating at 45 kV and 40 mA.

Tensile adhesion test: The tensile adhesion between the coating and the Ti substrate was measured using Quad-Romulus III system (Quad Group Inc., Pull Down Breaking point). The 3.5 mm diameter studs that were pre-coated with a thin layer of epoxy by manufacturer (Quad Group Inc) were mounted perpendicularly on each of the coated surface of the 10 Ti discs using spring mounting clips. The mounting clip allowed the stud to be perpendicular to the coating surface under a constant pressure during the curing procedure of epoxy. The discs were then placed in an oven and the epoxy was cured at 150° C. for 1 h. The loading rate of the tensile test was at 2N/sec and the tensile strength was measured in MPa. The above method is well-validated in industrial Quality Control laboratories for measuring the adhesion strength of thin films and complies with Mil. Std 883 standard test methods. The pre-coated epoxy layer on the stud was thin preventing the penetration of resin to substrate and applies a homogenous resin thickness on the coating. After removing the apatite coating, the samples were analyzed under SEM and EDS to ensure that the epoxy did not penetrated to the Ti substrate. ASTM C633, the standard procedure for measuring the adhesion of HA-plasma-sprayed coating, could not be used in this study because the ASTM procedure can be only applied in coating thickness greater than 0.38 mm.

Scratching test: The scratch test is a common technique used to evaluate the adhesion of a thin coating on the substrate. The adhesion of the coatings obtained in our study was assessed using a CSEM Revetest scratch tester fitted with a Rockwell C 200 µm-radius diamond stylus. The point of adhesion failure of the coating from the substrate was detected by an increase in the acoustic signal from the sample. This load is called the critical load Lc or failure load measured in N and corresponds to the bonding strength between the coating and substrate. The scratches were generated on the samples by constantly increasing the load at the rate of 100 N/min while the sample was displaced at the constant speed of 10 mm/min. The critical load of coating was measured 10 times.

Results

Figure 2:
FIGS. 2A and 2B show SEM micrographs of monetite coating at low (A) and high (B) magnifications. The monetite crystals were large and rectangular and covered the entire Ti surface.
FIGS. 2C and 2D show SEM micrographs of the Apatite coating (after monetite-to-apatite transformation) at low (C) and high (D) magnifications. Small apatite crystals were agglomerated following the outline of the initially formed large monetite crystals.
FIG. 2E is a cross-section view of the apatite coating and demonstrates the porosity (p) and thickness of the coating.
Figure 2:
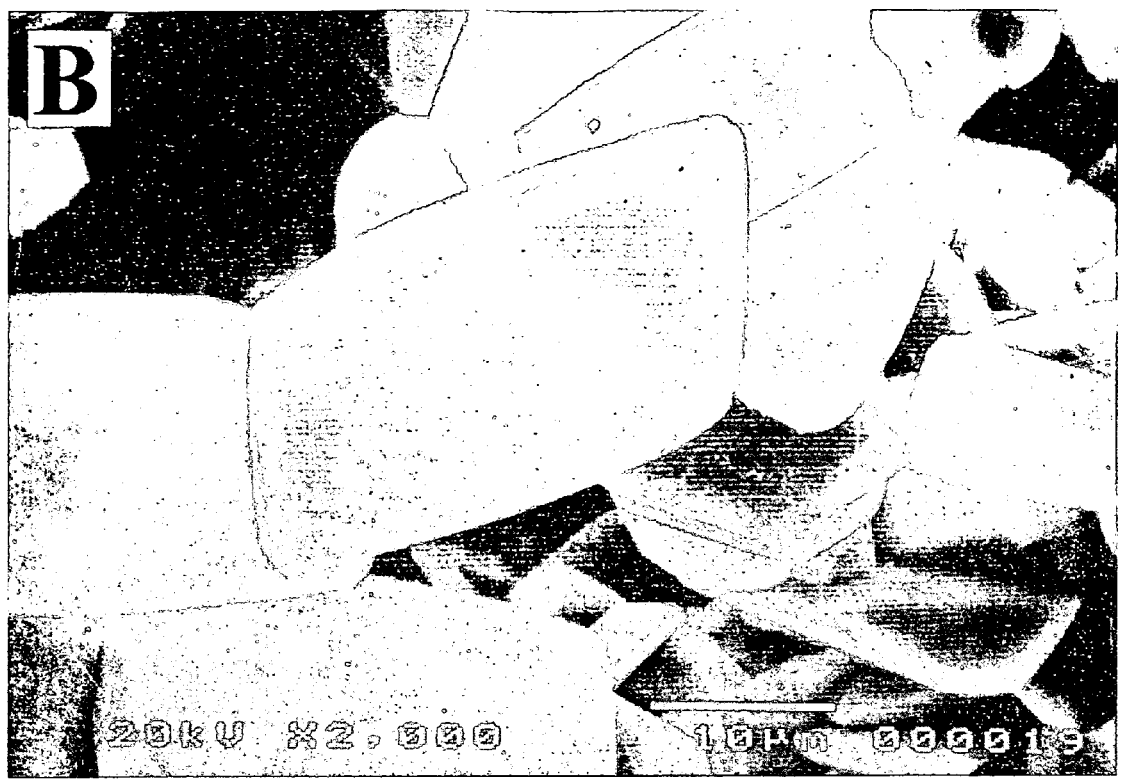
Figure 2:
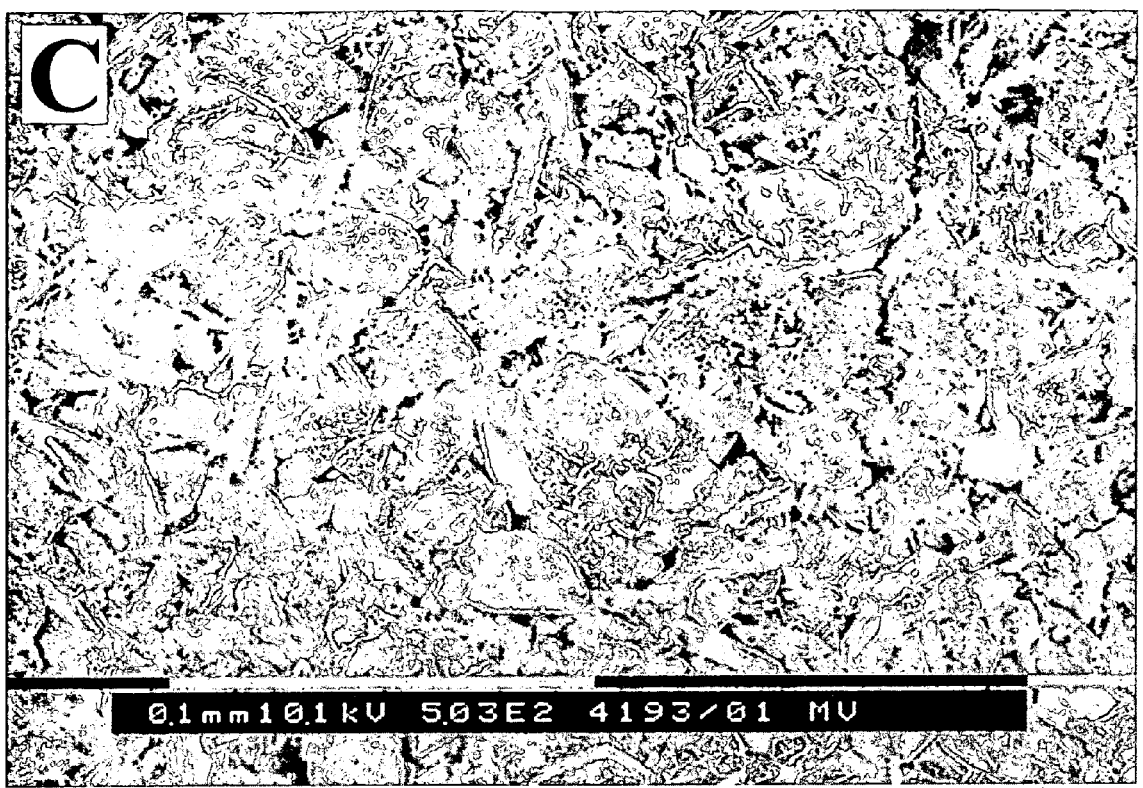
Figure 2:
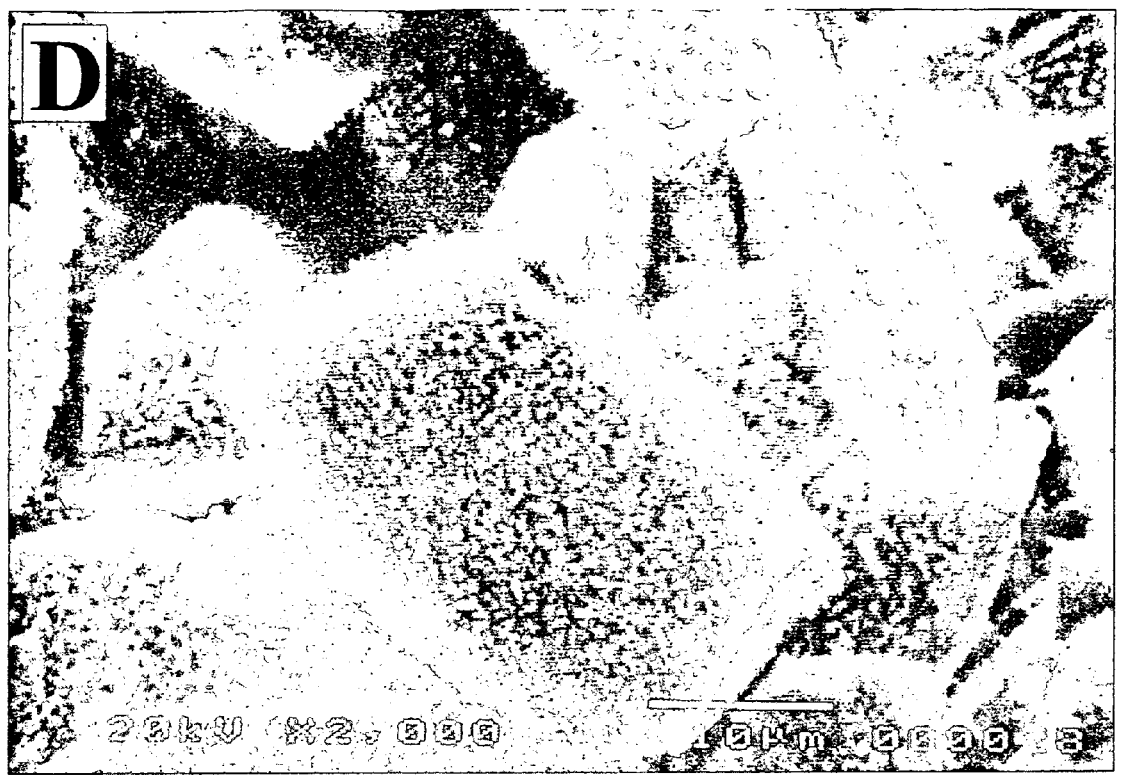
Figure 2:
Figure 3:
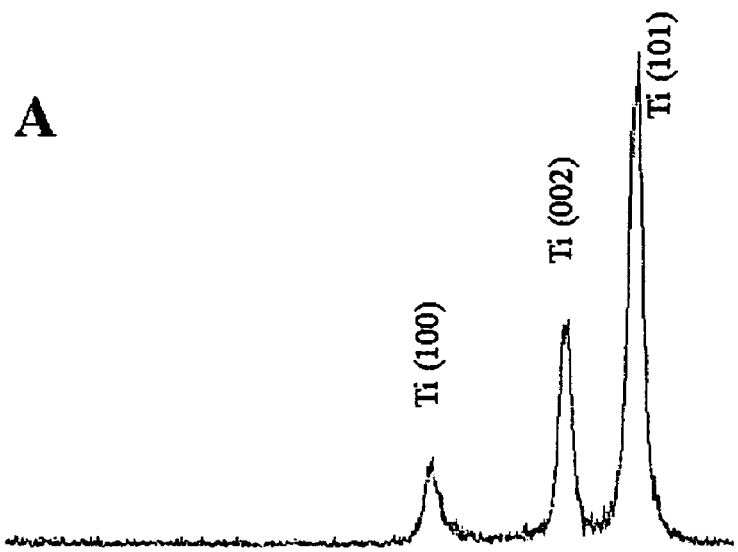
FIG. 3A depicts the X-ray diffraction pattern of a Ti surface (control group)
FIG. 3B is similar to 3A but shows the pattern for the monetite coating (first step of the coating process). The highest peak of monetite, (002) lattice plane, was located at $2\theta=26.5°$.
FIG. 3C is similar to 3A and 3B but shows the X-ray diffraction pattern of the apatite coating (second step of the coating process) with the highest peak of apatite, (211) lattice plane at $2\theta=31.8°$. Preferred orientation along the (002) lattice plane was observed for the apatite coating.
Figure 3:
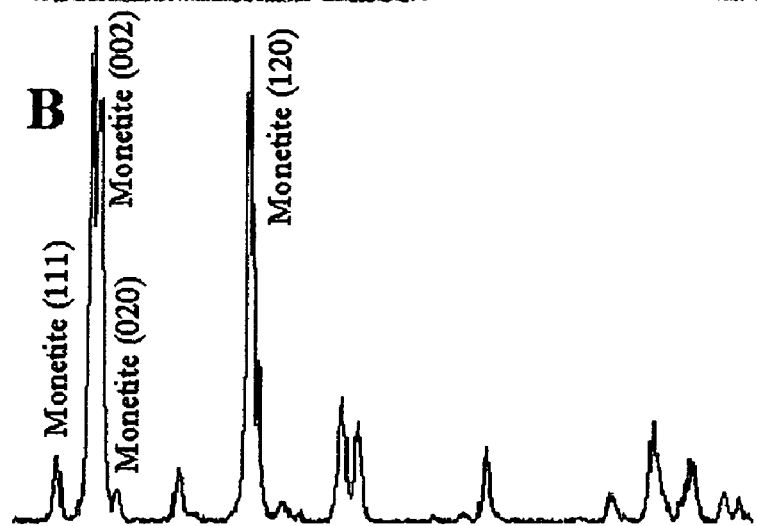
Figure 3:
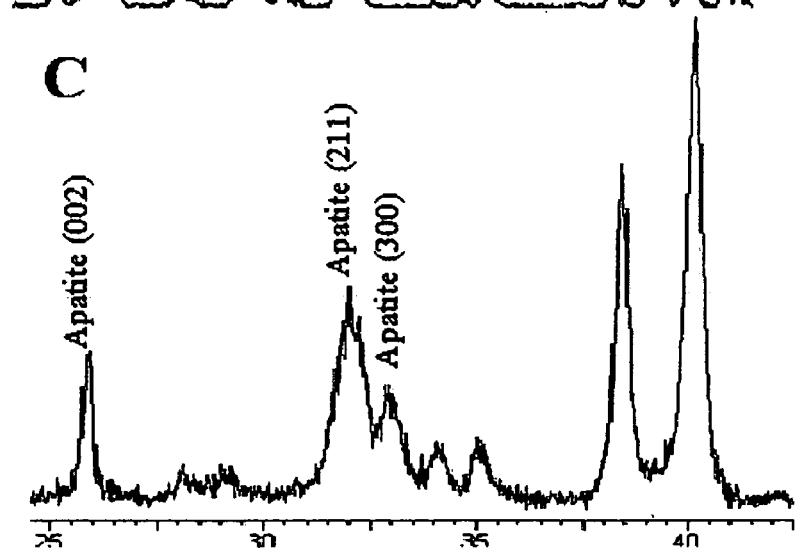

Formation of Calcium Phosphate Crystals from Acidic Solution of Calcium and Phosphate:

SEM analysis showed a uniform coating covering on the entire Ti surface after incubation in acidic calcifying solution (FIG. 1B compared to 1A). The Ca—P coating from acidic solution consisted of large and rectangular crystals (FIGS. 2A and 2B). XRD identified these crystals as dicalcium phosphate anhydrous (DCPA) or monetite, $CaHPO_4$, the highest peak located at $2\theta=26.5°$ (FIG. 3B). A preferred orientation along the (111) lattice planes of the monetite structure was observed from the XRD pattern (FIG. 3B). The ratio of the intensity of (111) plane to that of (020) in the diffraction pattern of the coating was about 2.5, compared to a ratio of 1.5 observed in the diffraction pattern of monetite powder (JCPDS# 71-1759). Higher intensity ratio in the coating compared to that in powder diffraction pattern indicates preferred orientation along in the monetite coating (111). Table 1 shows the levels (percentage) of different chemical elements identified in the monetite coating using EDS. The Ca/P atomic weight ratio from EDS was 1.16. Sodium (Na) was not detected in the monetite coating.

Transformation of Monetite to Apatite

In the second step, the discs coated with monetite obtained from the first step were immersed in NaOH solution at 75° C. for 24 h. XRD analysis showed that monetite coating was transformed to apatite, with the highest peak (211) at $2\theta=31.8°$ (FIG. 3D). The XRD pattern of apatite coating (FIG. 3C) showed (002)/(300) lattice planes intensity ratio of 1.5 compared to a ratio of 0.67 for the apatite powder (JCPDS# 09-0432), indicating preferred orientation along the (002) planes of the apatite crystals in the coating. The apatite crystals were agglomerated following the outline of the initially formed large monetite crystals (FIGS. 2C and 2D). SEM of the cross section of the coating showed porosity and a thickness of approximately 30 μm (FIG. 2E).

Table 1 summarizes the atomic percentage of Ca, P, and Na obtained using EDS analysis in different areas of the coating. The Ca/P ratio of the apatite coating was higher than that of the monetite coating (1.79 vs. 1.16). A low percentage of Na was detected in the apatite coating (Table 1), probably due to the partial incorporation of $Na^+$ ions into apatite structure (Na-for-Ca substitution) during the transformation of the monetite to apatite in NaOH solution.

TABLE 1

Concentrations of Ca, P, and Na (atomic %) in different areas of the coating.

| | Ca | P | Na | Ca/P | (Ca + Na)/P |
|---|---|---|---|---|---|
| On the coatings | | | | | |
| Monetite coating (FIG. 2A) | 53.66 ± 0.21 | 46.35 ± 0.21 | 0 | 1.16 ± 0.01[a] | 1.16 ± 0.01[a] |
| Apatite coating (FIG. 2C) | 60.75 ± 0.37 | 34.02 ± 0.3 | 5.23 ± 0.15 | 1.79 ± 0.03[b] | 1.94 ± 0.03[b] |
| After removing the apatite coating | | | | | |
| After removing the apatite coating using tensile test (FIG. 5A #1) | 58.50 ± 0.51 | 36.5 ± 0.46 | 5.00 ± 1.8 | 1.63 ± 0.04[c] | 1.74 ± 0.03[c] |
| After removing the apatite coating using tensile test (FIG. 5A #2) | 53.08 ± 2.60 | 36.87 ± 0.58 | 10.05 ± 1.71 | 1.44 ± 0.78[d] | 1.62 ± 0.04[d] |
| After removing the apatite coating using tensile test (FIG. 5A #3) | 49.98 ± 2.90 | 35.74 ± 0.73 | 13.28 ± 1.1 | 1.39 ± 0.82[d] | 1.78 ± 0.13[c] |
| After removing the apatite coating using scratching test (FIG. 5B #1) | 59.81 ± 0.62 | 34.38 ± 0.42 | 5.80 ± 0.15 | 1.74 ± 0.03[b] | 1.91 ± 0.03[b] |
| After removing the apatite coating using scratching test (FIG. 5B #2) | 56.42 ± 1.17 | 36.08 ± 1.45 | 7.62 ± 0.27 | 1.56 ± 0.09[c] | 1.78 ± 0.11[c] |
| After removing the apatite coating using scratching test (FIG. 5B #3) | 52.23 ± 3.77 | 36.52 ± 2.87 | 11.39 ± 2.16 | 1.43 ± 0.22[d] | 1.74 ± 0.22[c] |

Tukey statistical test to compare Ca/P and (Ca + Na)/P ratios in different areas (these ratios were compared separately for each area). Significant differences (p < 0.05) between a, b, c, and d. (The numbers on the FIGS. 5A and B correspond to the areas on which the EDS analyses were carried out).

Tensile and Scratch Test

Figure 4:
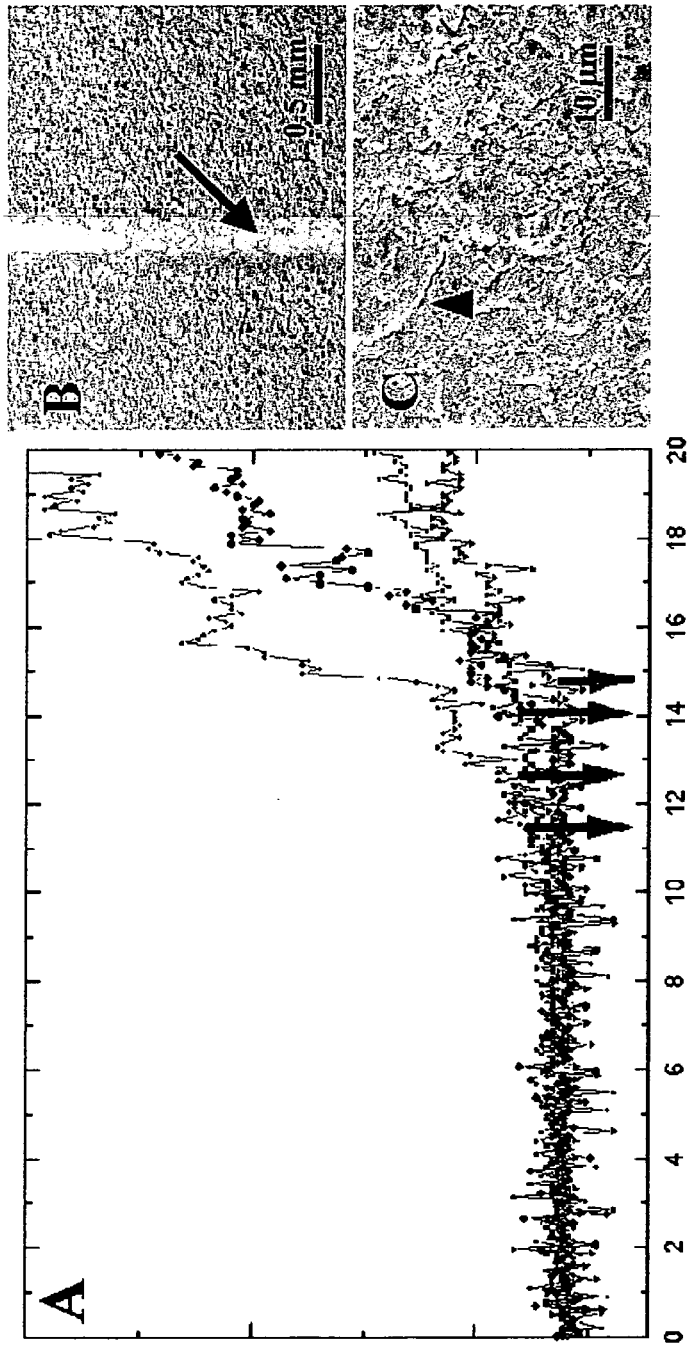
FIG. 4A depicts critical load (failure load) of four different measurements on the apatite coating. The critical load was detected from the first increase in acoustic signal (arrows).
FIG. 4B shows a scratch track on the coating, showing no fracturing or chipping inside or at the border of the track. The critical load was at the point where the coating was removed and the Ti surface became visible (arrow).
FIG. 4C is a higher resolution of the track and shows the presence of very small lateral cracks (delta) and coating delamination inside the coating before the failure point.

FIG. 4A shows the scratch test data plotted for four different measurements. Scratches made on each coating were reproducible in the failure mode. The failure load (critical load) at which the coating starts to be removed and the Ti surface to become visible was measured at the point of the first increase in acoustic signal from the Ti surface (arrows in FIG. 4A and FIG. 4B). The average of failure load of the coating was 13.1±1.3N. FIGS. 4B and 4C show the scratch track on apatite coating. No fracture or chipping was observed at the border or inside the scratch track and the coating materials were squashed along of the track. Just before the point of the removal of the coating from the substrate, small lateral tensile cracks were observed inside of the scratch track (FIG. 4C).

Figure 5:
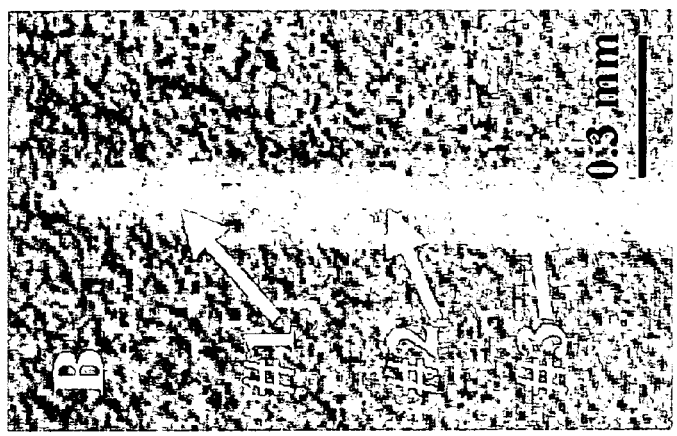
FIG. 5A shows an SEM micrographs of coating residues after the tensile test.
FIG. 5B shows the residue of the scratch test. The numbers on the FIGS. 5A and 5B correspond to the areas on which the EDS analyses were carried out (Table 1).
Figure 5:

The mean tensile strength in different areas of the coating was 5.2±2.1 MPa. No trace of epoxy was detected on substrate after coating removal demonstrating the absence of penetration of the resin to the substrate. SEM and EDS analysis showed—evidence of the presence of—coating residues on the areas from which the coating was removed during the tensile and scratch tests (FIGS. 5A, 5B and Table 1). Even after the coating appeared visually to have been removed, EDS demonstrated the presence of calcium and phosphorous elements on the Ti surface. The numbers on FIGS. 5A and 5B correspond to the areas on which the EDS analysis was performed. After the tensile test, the Ca/P ratio of the coating residues in different areas was significantly lower (P<0.05)

than that of coating surface (Table 1). Decreasing Ca/P ratio was also observed in the coating towards the Ti substrate in the scratch track of the scratching test (Table 1). Considering a Na-for-Ca substitution in the apatite, (Ca+Na)/P ratio would give a better estimation of the calcium phosphate phase of the coating. Although the percent of Na increased in the coating residues, the (Ca+Na)/P ratio was still lower in the coating residues close to the substrate compared to that away from the substrate and closer to the surface (Table 1). EDS analysis of the Ti surface (after removing the apatite coating) demonstrated the presence of Ca—P compounds as well as a higher percentage of Na—. The higher percentage of Na on titanium surface could be due to the formation of Na titanate during the monetite-to-apatite transformation in NaOH solution at 75° C.

Discussion

Coating Composition and Structure

The foregoing results show that homogenous and adherent Ca—P coating (monetite) formed on titanium discs during the immersion of the substrates in the acidic calcifying solution. The low pH of the calcifying solution has several effects on the coating procedure. The low pH of the solution permitted higher a concentration of the calcium and phosphate ions in the calcifying solution. In a neutral calcifying solution (pH 7), the concentrations of calcium and phosphate ions are limited and at higher concentrations, Ca—P crystals start to precipitate in the solution. Using a calcifying solution containing a higher concentration of calcium and phosphate results in a better coverage of the deposited Ca—P coating. An acidic solution also affects the topography and chemistry of the Ti surface. Several studies have reported the effects of various acids on topography and chemistry of titanium surface. [Kim W D. Effects of Acid Treatments on in vitro Bioactivity of Titanium. M.S. Thesis, New York University 2002.] Acid etching could improve bone/implant attachment by improving the mechanical interlock between the implant and the host bone. Surface topography has also been shown to have an effect on osteoblasts cell morphology, proliferation, and differentiation. [Boyan B D, Lohmann C H, Dean D D, Sylvia V L, Cochran D L, Schwartz Z. Mechanisms involved in osteoblast response to implant surface morphology. Annu Rev Mater Res 31:357-371, 2001; Poisoned L, Reybier K, Jaffrezic N, Comte V, Lagneau C, Lissac M, Martelet C. Relationship between surface properties (roughness, wettability) of titanium and titanium alloys and cell behaviour. Mat Sci Eng C-Bio S 23:551-560, 2003] Acid etching creates pits and increases the surface roughness and surface area of implant. Higher surface area could improve the adsorption of proteins and growth factors on materials that in turn may affect cells behavior. On the other hand, a rougher surface could provide a higher number of nucleation sites for the growing calcium phosphate crystals, thereby improving both coverage and adhesion of the coating due to the mechanical bonding between the coating crystals and the Ti surface. Both acid and alkali pre-treatment have been shown to increase the thickness of oxide layer on the Ti or Ti alloy surface. The titanium oxide plays a critical role on the absorption of organic layer (e.g. proteins) or mineral (e.g. calcium phosphate) on the Ti surface. In the presence of water, the titanium oxide layer becomes hydroxylated and forms Ti—OH groups. The Ti—OH groups on titanium surface are amphoteric, exhibiting both acidic and basic properties. Acidic hydroxide binds to two Ti atoms and basic hydroxide binds to one Ti atom. The following equations reactions show the acidic and basic reactions of Ti—OH with water molecule:

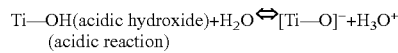
Ti—OH(acidic hydroxide)+H$_2$O ⇌ [Ti—O]$^-$+H$_3$O$^+$
(acidic reaction)

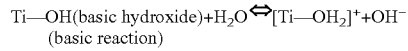
Ti—OH(basic hydroxide)+H$_2$O ⇌ [Ti—OH$_2$]$^+$+OH$^-$
(basic reaction)

Acidic hydroxide gives proton and causes a negative charged surface (acidic reaction), while basic hydroxide accepts proton and makes a positive charged surface (basic reaction). In an acidic solution (e.g., calcifying solution), the higher availability of protons promote more basic reactions occur causing a positively charged surface. On the other hand, in a basic solution, the proton detached from acidic hydroxide (acidic reaction) resulting in a negatively charged surface.

In our method, immersion of titanium discs in acidic calcifying solution could have resulted in a positive surface charge on the substrate, attracting the phosphate ions and creating the nucleation sites for calcium phosphate (monetite) deposition. Phosphoric acid used as of one of ingredient of calcifying solution provides phosphate groups (H$_2$PO$_4^-$, HPO$_4^{2-}$, and PO$_4^{3-}$), that could be attracted to the positive charge of [Ti—OH$_2^+$] and form—further nucleation sites for Ca—P deposition. Furthermore, acid treatment could also increase the thickness of TiO$_2$ layer. Higher roughness, thicker TiO$_2$ layer, and positively charged surface could all contribute to a higher attachment of the monetite layer formed from acidic calcifying solution. It should be mentioned that the higher concentration of positive charge reduces the calcium concentration on titanium surface and also decreases the substitution of phosphate ions for the basic hydroxide group. As mentioned above, in acidic solution, the equilibrium of basic reaction is shifted to right side resulting in a lower number of basic hydroxide present on the Ti surface.

Depending on the pH, temperature, and composition of the calcifying solution, different types of Ca—P compounds can form or transform from one type to another type. For example, under acidic condition (pH 2 to 5) and at low temperature (25° C. to 60° C.) dicalcium phosphate dihydrate (DCPD), CaHPO$_4$.2H$_2$O is the preferred Ca—P phase. Under the conditions of our method (pH 2, 75° C.), monetite or dicalcium phosphate anhydrous (DCPA), CaHPO$_4$, was the stable Ca—P phase. Monetite converted to apatite crystal in a basic solution, as demonstrated in earlier studies. LeGeros R Z. Calcium Phosphates in Oral Biology and Medicine. Volume 15. San Francisco: Karger; 1991. 201 p.; [LeGeros R Z. The unit-cell dimensions of human enamel apatite: effect of chloride incorporation. Arch Oral Biol 20:63-71, 1974.; LeGeros R Z, LeGeros J P, Trautz O R, Shirra W P. Conversion of monetite, CaHPO4 to apatites: effect of carbonate on the crystallinity and the morphology of apatite crystallites. Adv X-ray Anal 14:57-66, 1971]. The transformation of one type of calcium phosphate to another type is in fact a dissolution/re-precipitation process. [LeGeros R Z. Calcium Phosphates in Oral Biology and Medicine. Volume 15. San Francisco: Karger; 1991. 201 p.; The initial Ca—P phase dissolves in acidic or basic solutions and the second phase re-precipitates from the supersaturated solution. The SEM micrographs showed that the apatite crystals precipitated following the outline of the initially formed monetite crystals, in a similar manner as that observed for the transformation of octacalcium phosphate, OCP, to apatite.

EDS analysis showed the presence of Na$^+$ ions in the apatite coating but was not detected in the monetite coating indicating that Na-for-Ca substitution occurred in the apatite during the transformation of monetite to apatite in the NaOH solution. The Ca/P molar ratio of the apatite coating was calculated as 1.79. However, when Na-for-Ca substitution in the apatite was considered, the (Ca+Na)/P molar ratio was calculated as 1.94. The Ca/P molar ratio of stoichiometric hydroxyapatite, $Ca_{10}(PO_4)_6(OH)_2$, is 1.67, lower than that calculated for the apatite coating in this study. The higher value of the Ca/P molar ratio obtained for the coating may be due to the partial substitution of carbonate for phosphate (carbonate type B). The Ca/P molar ratio for the monetite coating was calculated as 1.16, slightly higher than that of a stoichiometric monetite, $CaHPO_4$, with a Ca/P molar ratio of 1.0.

EDS analysis obtained from areas from which the apatite coating was removed or scratched off demonstrated the presence of a calcium phosphate phase but with at a lower (Ca+Na)/P or Ca/P ratio compared to that of the intact coating surface (Table 1). Lower Ca/P ratio of the coating materials at the coating/Ti interface could be due to positive surface charge (formed because of acidic calcifying solution), that attracts more phosphate ions and leads to a lower Ca/P ratio. Compared to the apatite coating surface, the percentage of Na was higher on the Ti surface or coating residues after removing or scratching off the apatite coating. The higher percentage of Na on titanium surface or in the coating layer closer to substrate may be explained by the partial incorporation of Na in the apatite structure (Na-for-Ca substitution) during the transformation of monetite to apatite in the NaOH solution and by the formation of Na titanate layer on titanium surface[29] during the monetite-to-apatite transformation. The higher percentage of Na could be in fact due to the higher percentage of Na on the titanium substrate and not in the remaining apatite coating. Formation of Na titanate at the substrate/coating interface could also cause an increase in the coating adhesion.

Coating/Substrate Bonding

The tensile strength of apatite coating prepared in the foregoing was about 5.2 MPa. Tensile strength of plasma-sprayed coating has been reported to range from about 5 to 54 MPa. This wide range of tensile strength values reported for plasma-sprayed HA coating may be due to the penetration of the resin to the Ti substrate used in the tensile test (especially with thin or porous coatings) leading to inaccurate measurements. Another source of inaccuracy in measuring tensile strength of the plasma-sprayed HA coating could be the misaligning of the tensile force causing a partially shear force during the measurement of tensile strength. In our method, it was observed that the failure occurred within the coating itself rather than at the coating/titanium interface, indicating low cohesive strength of coating compared to its adhesive strength on titanium surface. Even for the samples on which the coating was visually removed, EDS revealed the presence of remaining Ca—P crystals on titanium surface.

The coating adhesion using CSEM scratch test was measured at about 13.1±1.3N. This value was much higher than those reported for sputtering and laser deposition coatings which were 38.47 mN and 1.7 mN respectively, using 50 µm-radius stylus. [Inagaki M, Yokogawa Y, Kameyama I. Bond strength improvement of hydroxyapatite/titanium composite coating by partial nitriding during RF-thermal plasma spraying. Surf Coat Tech 173:1-8, 2003. Ozeki K, Yuhta T, Fukui Y, Aoki H, Nishimura I. A functionally graded titanium/hydroxyapatite film obtained by sputtering. J Mater Sci-Mat Med 13:253-258, 2002.] Whereas for HA coating prepared using electrochemical deposition, 20N was needed to scraped off the coating from the substrate. [Kuo M C, Yen S K. The process of electrochemical deposited hydroxyapatite coatings on biomedical titanium at room temperature. Mat Sci Eng C-Bio S 20:153-160, 2002.] It should be noted that the results of scratch test varies as a function of the coating thickness, coating ductility and brittleness, shape and size of stylus, the rate of applying the load, and substrate hardness. In our study the coating was squashed and displaced to both sides of the scratch track, without any chipping, or fracturing. The acoustic signal started to increase (the point of reading the critical load) at the point when the coating started to be removed from the substrate and the Ti surface became visible (adhesive failure). Before the failure point of the coating, small lateral cracks were observed inside the track due to coating delamination. The absence of fracturing indicates that the coating materials were squashed without detaching from the substrate. Fernandez-Pardas et al [Fernandez-Pradas J M, Cleries L, Martinez E, Sardin G, Esteve J, Morenza J L. Influence of thickness on the properties of hydroxyapatite coatings deposited by KrF laser ablation. Biomaterials 22:2171-2175, 2001]. reported that when the coating deform without fracturing, and did not detach from the substrate even when subjected to 18N load. Squashing of coating materials without fracturing could be the reason for the big difference between the critical loads measured in our study compared to those reported for the other type of coating. For the coating prepared by Pulsed Laser Deposition technique, Arias et al. [Arias J L, Mayor M B, Pou J, Leng Y, Leon B, Perez-Amor M. Micro- and nano-testing of calcium phosphate coatings produced by pulsed laser deposition. Biomaterials 24:3403-3408, 2003] reported that although the first increase in acoustic signal was read at 3.5N (due to the formation of fractures), the coating was partially removed and the substrate became visible at 9.6N load. The adhesion of the coating obtained from our method was much higher than that of coating prepared in calcifying solution at 37° C. and pH 7.2. As mentioned above positive surface charge of titanium and higher surface roughness (both due to acidic pH of calcifying solution) could increase the number of nucleation site for monetite deposition. Phosphate groups ($H_2PO_4^-$, $HPO_4^{2-}$, and $PO_4^{3-}$) provided by phosphoric acid and $NaH_2PO_4.H_2O$ could bond to $[Ti-OH_2]^+$ group, create nucleation sites and increase the attachment of the calcium phosphate coating. Furthermore, formation of Na titanate during the transformation of monetite to apatite in NaOH solution, could also contribute to a higher coating/substrate adhesion.

CONCLUSION

The foregoing demonstrates the value of chemical deposition from acidic calcifying solution as an alternative coating technique. The coatings prepared using the present method were porous and composed of crystalline phase of apatite. Good coating adhesion was obtained compared to other low temperature coating methods. In our method, using dilute phosphoric acid in calcifying solution made a positive surface charge $[Ti-OH_2]^+$ which bonds to the phosphate groups ($H_2PO_4^-$, $HPO_4^{2-}$, and $PO_4^{3-}$) and provides more nucleation sites for calcium phosphate deposition. Furthermore, acidic calcifying solution could also modify the Ti surface topography and increase the mechanical interlock between the substrate and Ca—P coating. Formation of Na titanate during the transformation of monetite crystals to apatite could also favor apatite deposition and adhesion.

While the present invention has been set forth in terms of specific embodiments thereof, the instant disclosure is such that numerous variations upon the invention are now enabled to those skilled in the art, which variations yet reside within the scope of the present teaching. Accordingly, the invention is to be basically construed and limited only by the scope and spirit of the claims now appended hereto.

The invention claimed is:

1. A method for chemically depositing without the use of electrical potential an adherent bioactive calcium phosphate coating on a titanium or titanium alloy substrate comprising immersing the substrate in an acidic calcium phosphate calcifying solution having a Ca:P molar ratio in the range of 1/1 to 3/1, to form a non-apatitic calcium phosphate coating on the substrate wherein the temperature of the calcifying solution is in the range of 25° C. to 75° C.

2. A method in accordance with claim 1, wherein the pH of said calcifying solution is in the range of 2.1 to less than 7.0.

3. A method in accordance with claim 2, wherein the pH of said calcifying solution is in the range of 2.1 to 5.

4. A method in accordance with claim 1, wherein the temperature of the calcifying solution is in the range of 25° C. to 40° C.

5. A method in accordance with claim 2, wherein the temperature of the calcifying solution is in the range of 25° C. to 40° C.

6. A method in accordance with claim 5, wherein the time of immersion is in the range of from about 2 to 24 hours.

7. A method in accordance with claim 6, wherein the resulting non-apatitic calcium phosphate is one or more calcium phosphate compounds selected from the group consisting of DCPD, DCPA, and OCP.

8. A method in accordance with claim 1, wherein fluoride ions are included in said calcifying solution to render the resulting coating less reactive.

9. A method in accordance with claim 5, wherein the said time of immersion is controlled to provide a desired thickness for said coating.

10. A method in accordance with claim 9, wherein fluoride ions are included in said calcifying solution to render the resulting coating less reactive.

11. A method in accordance with claim 9, further including a subsequent step of immersing the coated substrate into a basic or neutral solution to convert the said coating into an apatite.

12. A method in accordance with claim 11, wherein the said solution used in said subsequent step has a pH of 7 to 12.

13. A method in accordance with claim 12, wherein the said solution used in said subsequent step has a temperature of from about ambient to 70° C.

14. A method in accordance with claim 13, wherein the said substrate is immersed in said solution used in said subsequent step for a period of from about 2 to 24 hours.

15. A method for chemically depositing without the use of electrical potential an adherent bioactive calcium phosphate coating on a titanium or titanium alloy substrate comprising immersing the substrate in an acidic calcium phosphate calcifying solution to form a non-apatitic calcium phosphate coating on the substrate; the pH of said solution being in the range of 2.1 to 5, and the temperature of said solution being in the range of from 25° C. to 40° C.

16. A method in accordance with claim 15, wherein the time of immersion in the solution is controlled to provide a desired thickness of said coating.

17. A method in accordance with claim 15, including a subsequent step of immersing the coated substrate into a basic or neutral solution to convert the said coating into an apatite.

18. A method in accordance with claim 17, wherein the said solution used in said subsequent step has a pH of 7 to 12.

19. A method in accordance with claim 18, wherein the said solution used in said subsequent step has a temperature of from about ambient to 70° C.

20. A method in accordance with claim 19, wherein the said substrate is immersed in said solution used in said subsequent step for a period of from about 2 to 24 hours.

21. A method in accordance with claim 1 or 15 wherein the acidic calcium phosphate calcifying solution comprises a calcium salt and a phosphate compound.

22. A method in accordance with claim 21 wherein the calcium salt is $CaCO_3$.

* * * * *